(12) United States Patent
Nagasaki et al.

(10) Patent No.: US 9,918,935 B2
(45) Date of Patent: Mar. 20, 2018

(54) COMPOSITION CONTAINING POLYCATIONIC TRIBLOCK COPOLYMER, POLYANIONIC POLYMER AND PHYSIOLOGICALLY ACTIVE PEPTIDE

(71) Applicant: UNIVERSITY OF TSUKUBA, Ibaraki (JP)

(72) Inventors: Yukio Nagasaki, Ibaraki (JP); Junya Kaneko, Ibaraki (JP); Toru Yoshitomi, Ibaraki (JP); Shiro Ishii, Ibaraki (JP)

(73) Assignee: UNIVERSITY OF TSUKUBA, A JAPANESE NATIONAL UNIVERSITY, Ibaraki (JP)

( * ) Notice: Subject to any disclaimer, the term of this patent is extended or adjusted under 35 U.S.C. 154(b) by 305 days.

(21) Appl. No.: 14/896,952

(22) PCT Filed: Jun. 10, 2014

(86) PCT No.: PCT/JP2014/065344
§ 371 (c)(1),
(2) Date: Dec. 9, 2015

(87) PCT Pub. No.: WO2014/199982
PCT Pub. Date: Dec. 18, 2014

(65) Prior Publication Data
US 2016/0175247 A1    Jun. 23, 2016

(30) Foreign Application Priority Data
Jun. 11, 2013   (JP) .................. 2013-123001

(51) Int. Cl.
*A61K 9/107*     (2006.01)
*A61K 38/44*    (2006.01)
(Continued)

(52) U.S. Cl.
CPC .......... *A61K 9/1075* (2013.01); *A61K 9/0019* (2013.01); *A61K 9/107* (2013.01);
(Continued)

(58) Field of Classification Search
CPC ........ A61K 9/107; A61K 38/44; A61K 38/28; A61K 38/38; A61K 9/00; A61K 47/34;
(Continued)

(56) References Cited

U.S. PATENT DOCUMENTS

2005/0112172 A1  5/2005 Pacetti
2011/0142787 A1  6/2011 Nagasaki et al.
(Continued)

FOREIGN PATENT DOCUMENTS

EP    2 808 349    12/2014
JP    2007-520260    7/2007
(Continued)

OTHER PUBLICATIONS

International Search Report dated Aug. 19, 2014 in International Application No. PCT/JP2014/065344.
(Continued)

*Primary Examiner* — Trevor Love
(74) *Attorney, Agent, or Firm* — Wenderoth, Lind & Ponack, L.L.P.

(57) ABSTRACT

[Problem] To provide a physiologically active peptide-loaded stable composition for injection into living bodies. [Solution] A composition containing a triblock copolymer represented by formula (I), a polyanionic polymer and a physiologically active peptide:

CNR-PEG-CNR    (I)

in the formula,
CNR moieties are each independently a polymer segment containing a repeating unit that contains, as a part of a
(Continued)

pendant group, a cyclic nitroxide radical bonded to a main polymer chain via a linking group that contains at least one amino group, and PEG is a segment that contains poly(ethylene glycol).

13 Claims, 9 Drawing Sheets

(51) Int. Cl.
| | |
|---|---|
| A61K 38/28 | (2006.01) |
| A61K 38/38 | (2006.01) |
| C08F 293/00 | (2006.01) |
| C08F 12/18 | (2006.01) |
| A61K 9/00 | (2006.01) |
| C08L 53/00 | (2006.01) |
| A61K 47/32 | (2006.01) |
| A61K 38/00 | (2006.01) |
| A61K 47/34 | (2017.01) |

(52) U.S. Cl.
CPC ............ *A61K 38/28* (2013.01); *A61K 38/385* (2013.01); *A61K 38/44* (2013.01); *A61K 38/443* (2013.01); *A61K 47/32* (2013.01); *A61K 47/34* (2013.01); *C08F 12/18* (2013.01); *C08F 293/005* (2013.01); *C08L 53/00* (2013.01); *A61K 38/00* (2013.01); *C08F 2438/02* (2013.01); *C08F 2438/03* (2013.01); *C12Y 101/03004* (2013.01); *C12Y 104/03003* (2013.01)

(58) Field of Classification Search
CPC ....... A61K 47/32; A61K 38/00; C08F 293/00; C08F 12/18; C08L 53/00
See application file for complete search history.

(56) References Cited

U.S. PATENT DOCUMENTS

2013/0330390 A1  12/2013  Pacetti
2014/0356315 A1  12/2014  Nagasaki et al.

FOREIGN PATENT DOCUMENTS

| JP | 2011-184429 | 9/2011 |
|---|---|---|
| JP | 2012-67025 | 4/2012 |
| JP | 2012-111700 | 6/2012 |
| WO | 2009/133647 | 11/2009 |
| WO | 2013/111801 | 8/2013 |

OTHER PUBLICATIONS 2012.3.2 PB-13 Min Ley Pua, Pennapa Chonpathompiunlert, Toru Yoshitomi, Yukio Nagasaki, "Novel redox flower micelle for chronic inflammation treatments", MANA International Symposium 2012, Tsukuba, Japan.

2012.6.7, Pua Min Ley, Pennapa Chonpathompiunlert, Toru Yoshitomi, Yukio Nagasaki, "Development of Novel Nitroxide Radical-Containing Injectable Hydrogels for Treating Chronic Inflammation", 65th meeting of Society for Free Radical Research Japan, Tokushima, p. 39, and English translation thereof.

2012.11.22 Pua Min Ley, Toru Yoshitomi, Pennapa Chonpathompiunlert, Aki Hirayama, and Yukio Nagasaki, "Redox Injectable Gel (RIG) for Treatments of Local Inflammation-Cattageenan-induced Arthritis-" International Workshop on Soft interface Science for Young Scientists (SIS YS 2012). Tsukuba, Japan.

2013.3.19-22 Pua Min Ley, Tom Yoshitomi, Pennapa Chonpathompiunlert, Aki Hirayama, and Yukio Nagasaki, "Redox-active Injectable Gel (RIG) for Treatments of Carrageenan-Induced Arthritis", 2nd International Conference on Biomaterials Science in Tsukuba (ICB S2013), Tsukuba, Japan, P155.

Atsushi Harada and Kazunori Kataoka (1998) "Novel Polyion Complex Micelles Entrapping Enzyme Molecules in the Core : Preparation of Narrowly-Distributed Micelles from Lysozyme and Poly(ethylene glycol)-Poly(aspartic acid) Block Copolymer in Aqueous Medium," Macromolecules 1998, 31, 288-294.

Shin-ichi Sawada, Kazunari Akiyoshi (2010) "Nano-Encapsulation of Lipase by Self-Assembled Nanogels : Induction of High Enzyme Activity and Thermal Stabilization," Macromolecular Bioscience 2010, 10, 353-358.

Extended European Search Report dated Oct. 13, 2016 in conesponding European patent application No. 14 81 0563.

[FIG. 1]
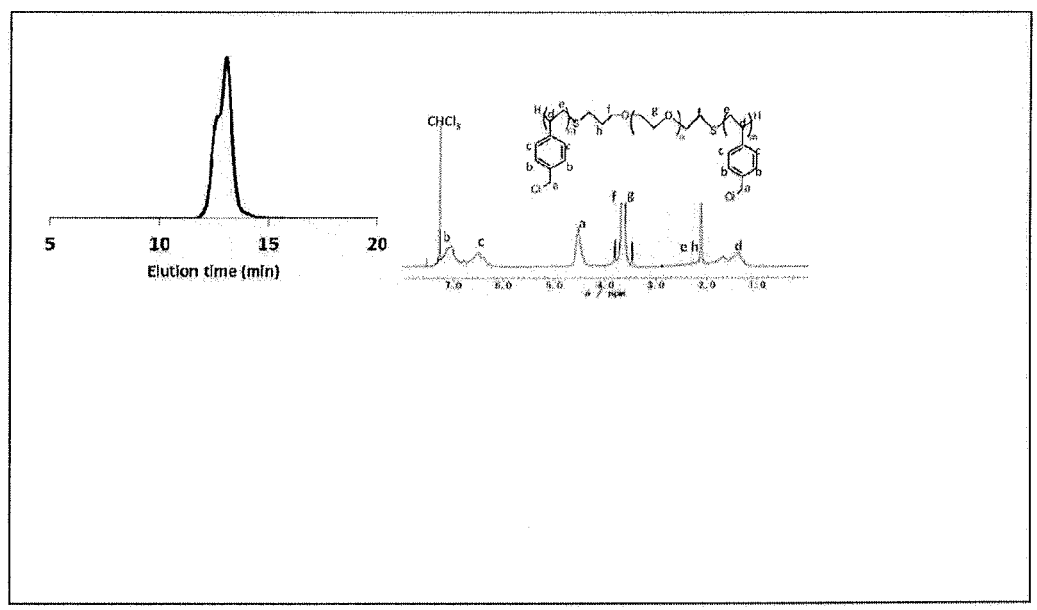
[FIG. 2]
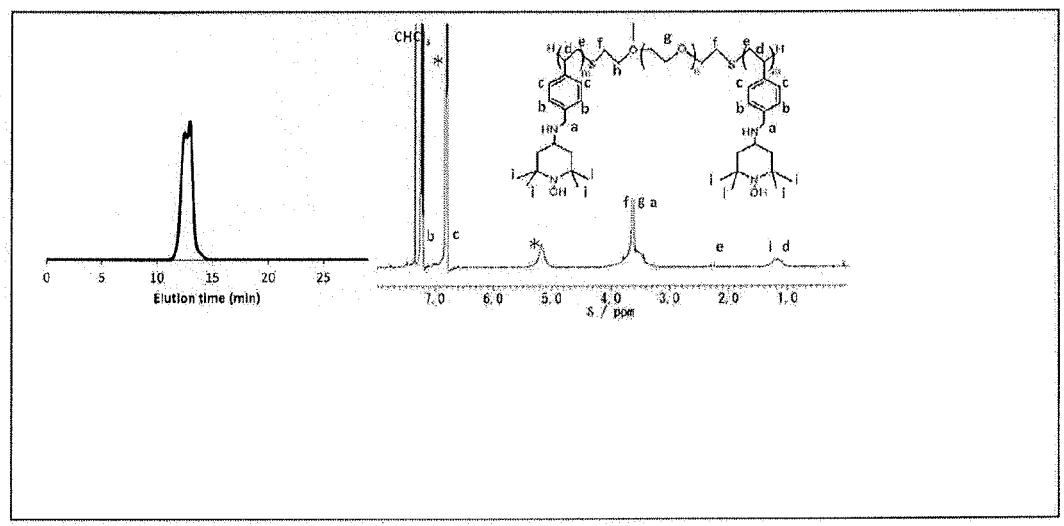

[FIG. 3]
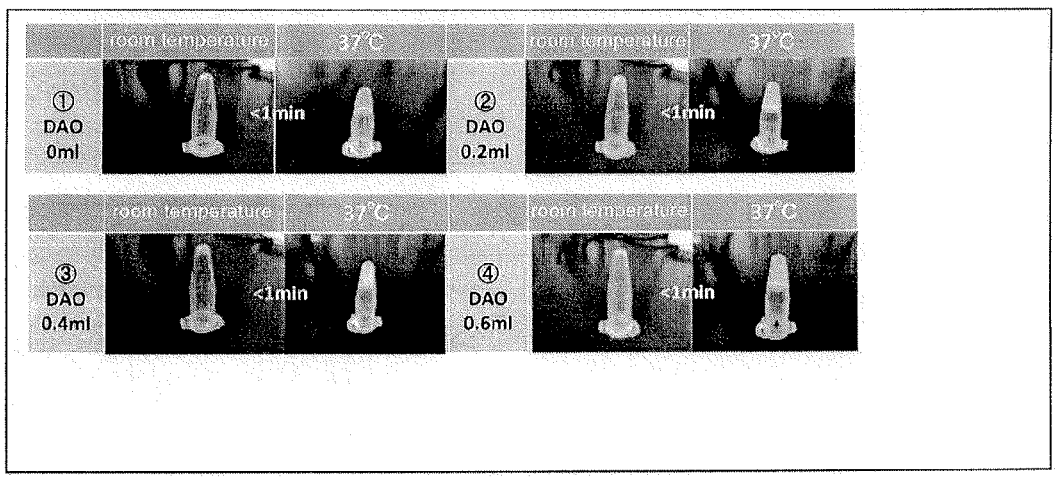
[FIG. 4]
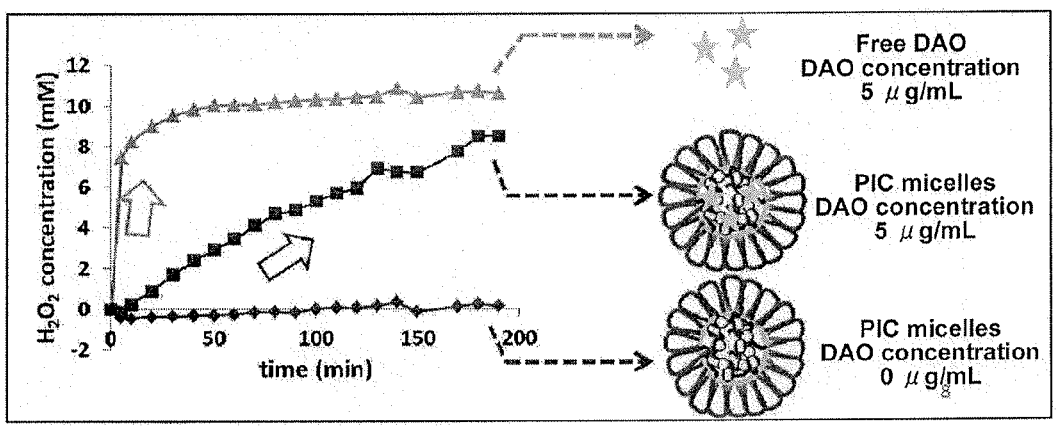

[FIG. 5]
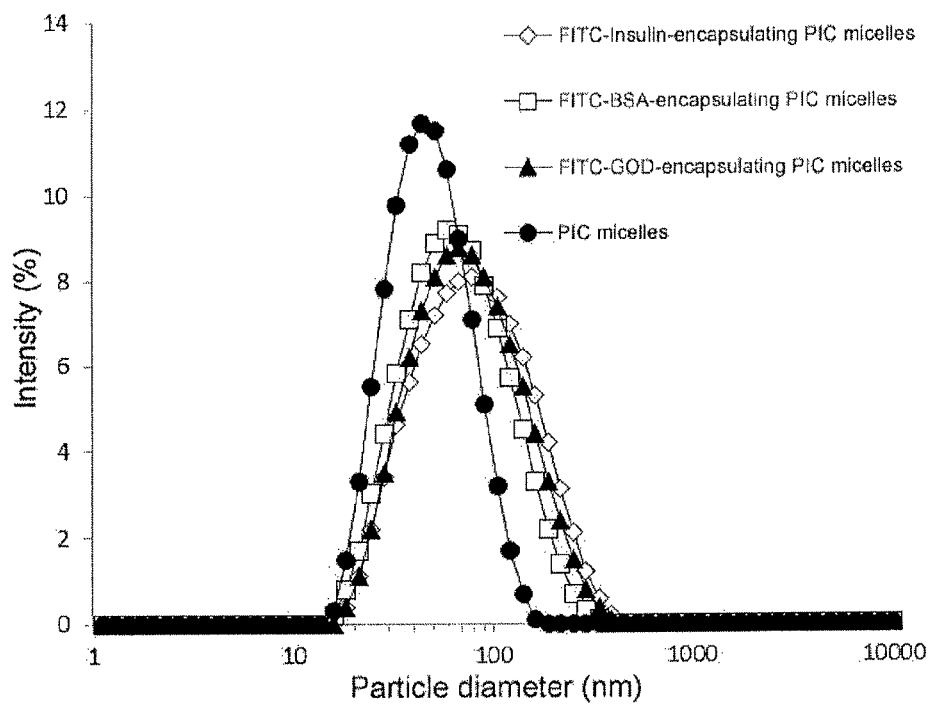
[FIG. 6]
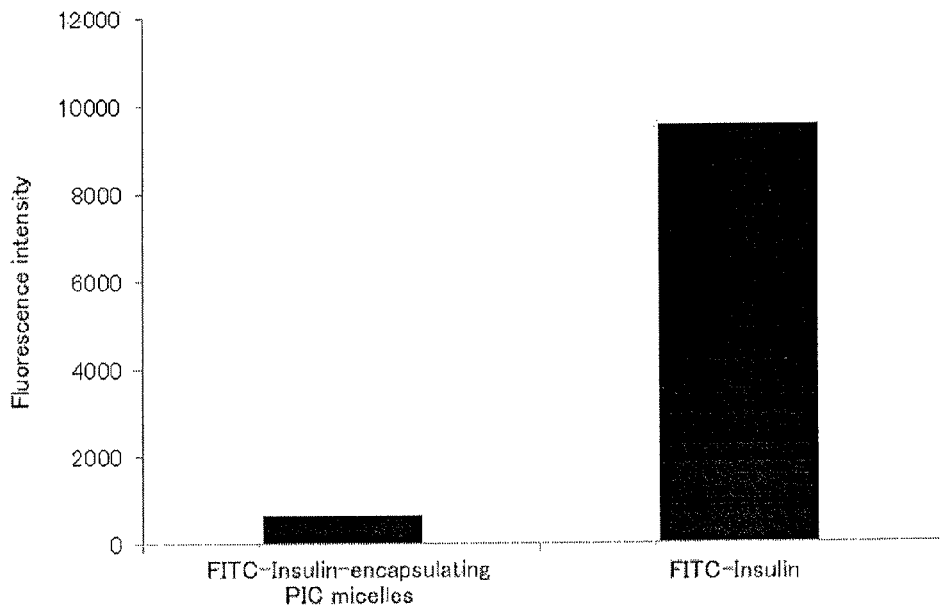

[FIG. 7]
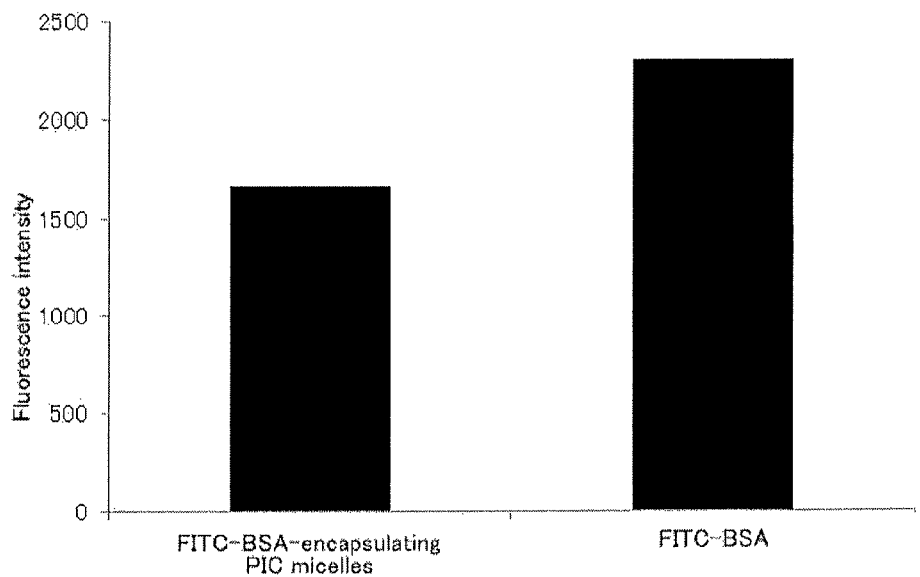
[FIG. 8]
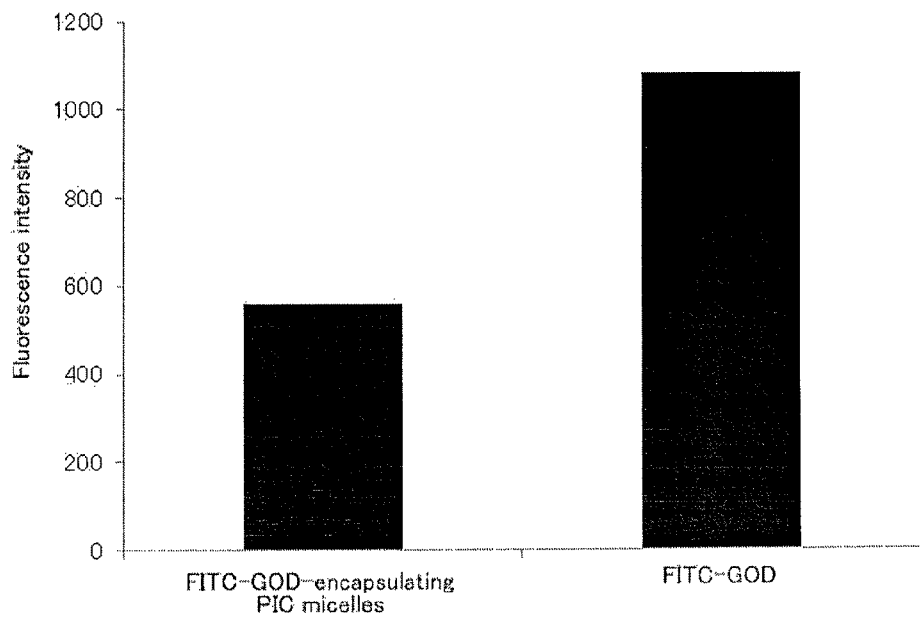

[FIG. 9]
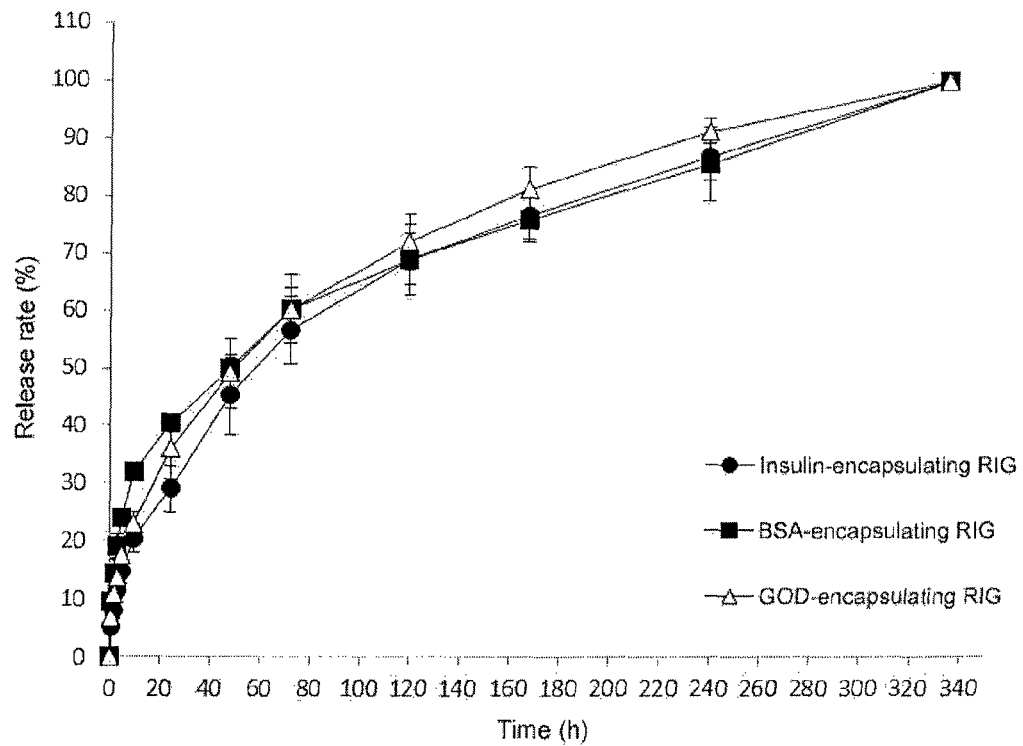
[FIG. 10]
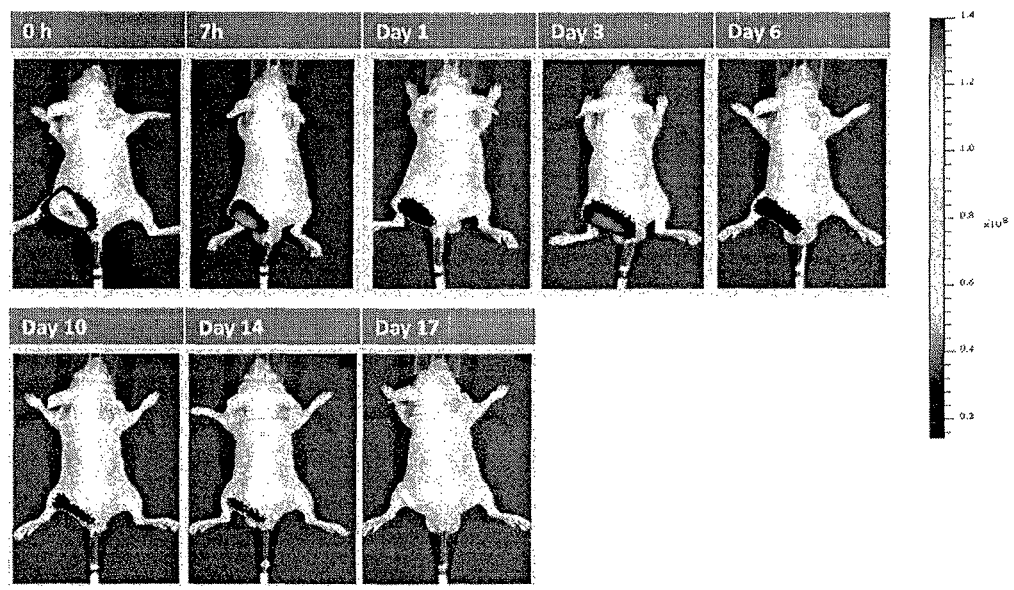

[FIG. 11]
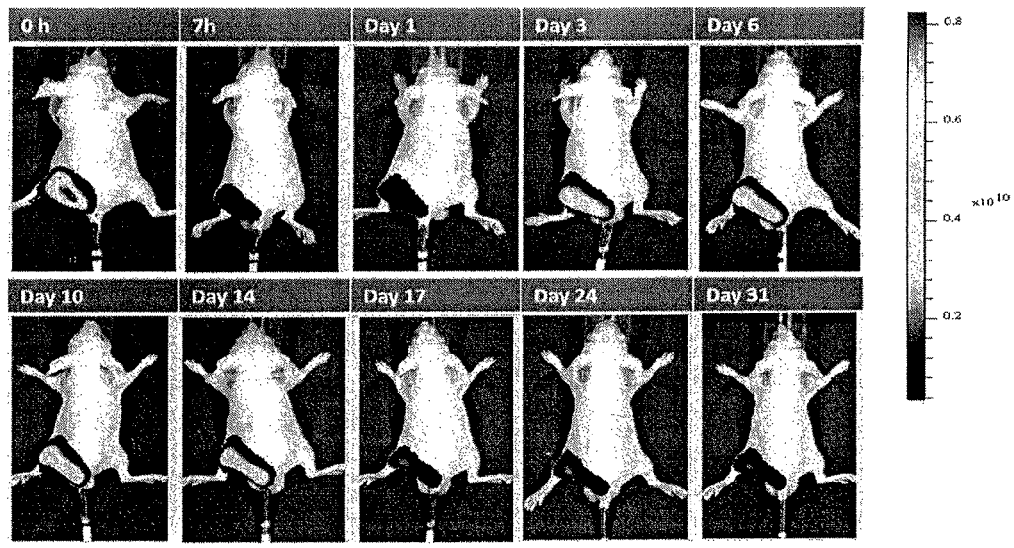
[FIG. 12]
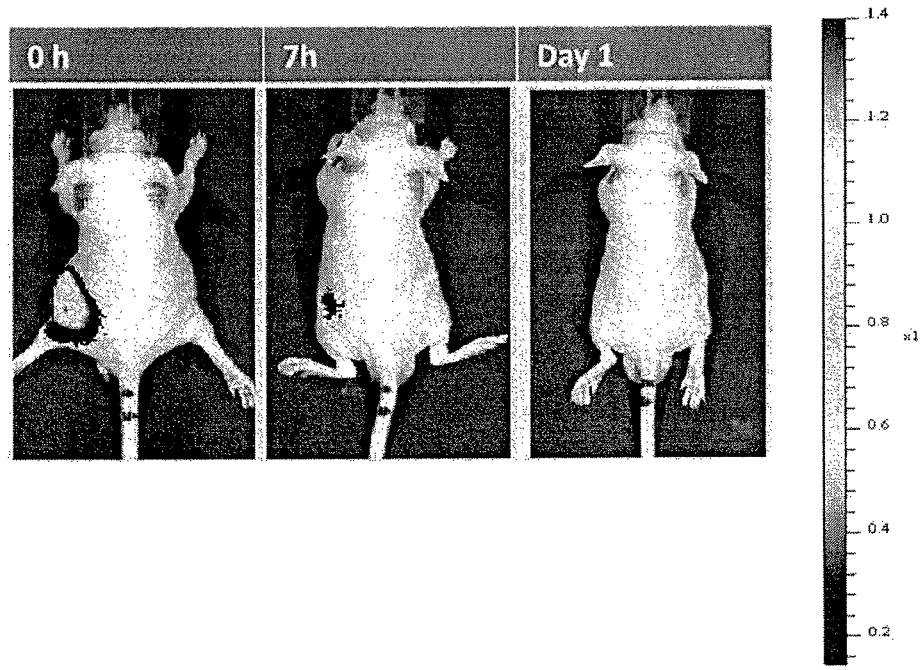

[FIG. 13]
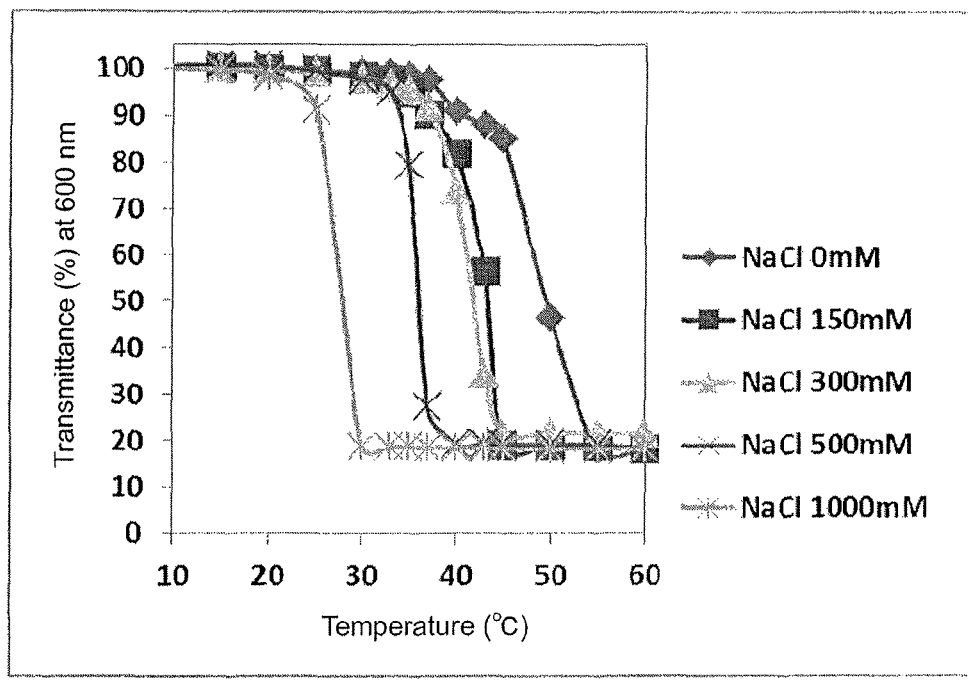
[FIG. 14]
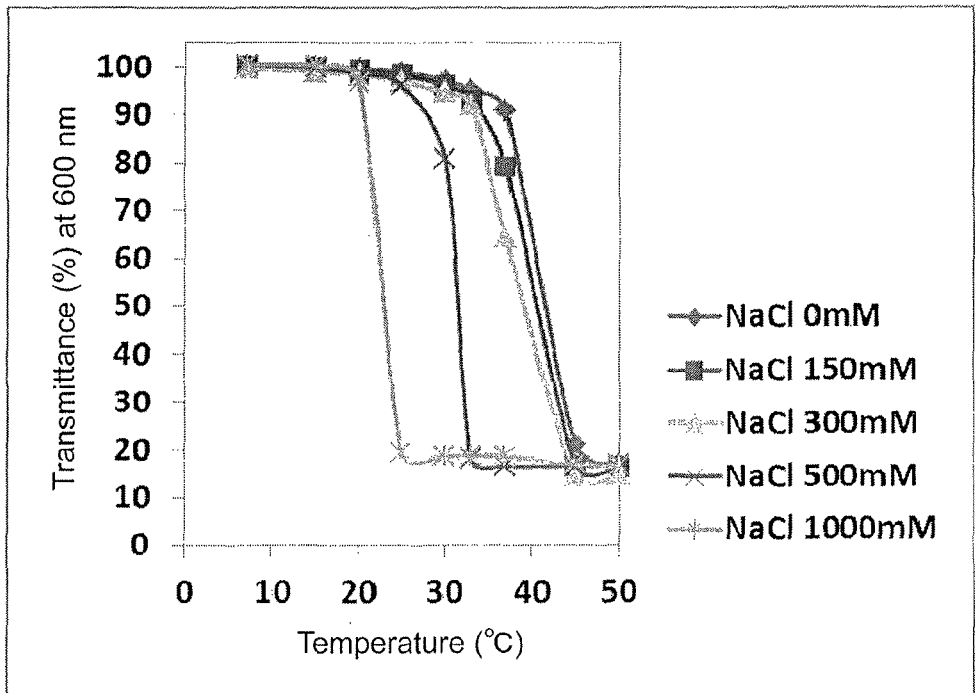

[FIG. 15]
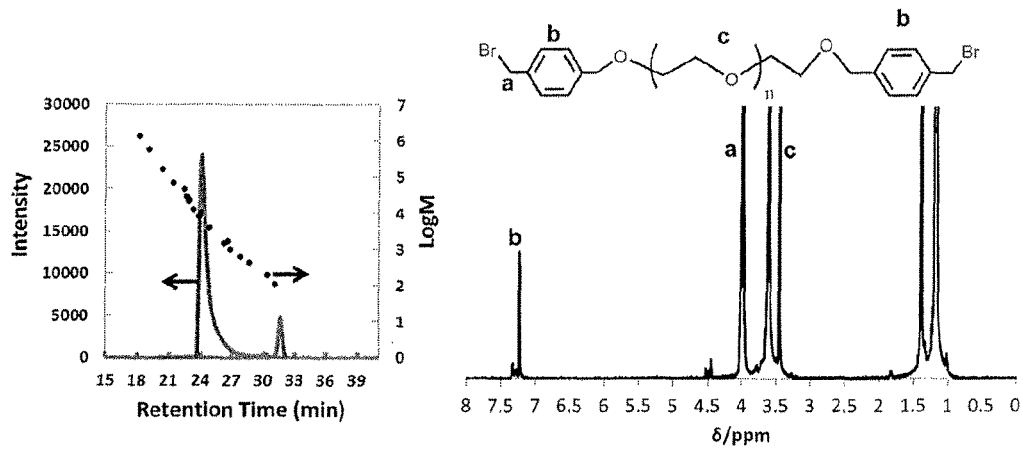
[FIG. 16]
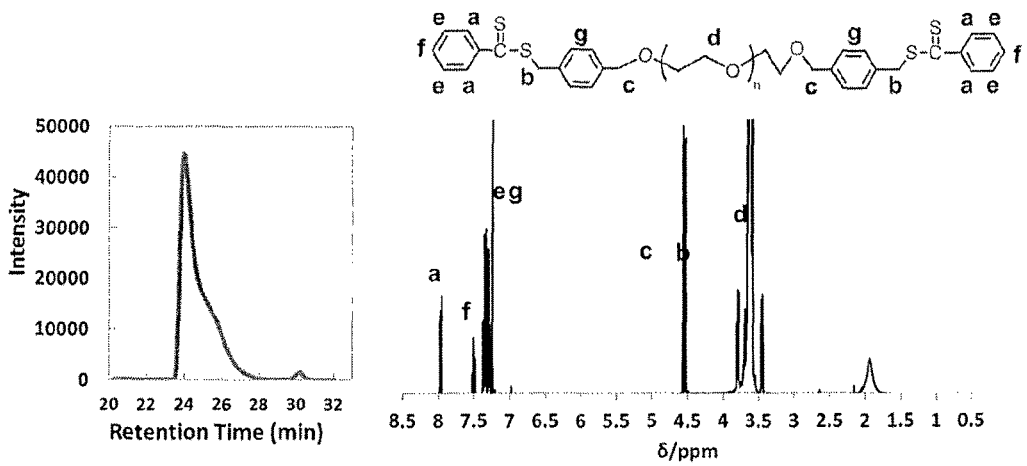
[FIG. 17]
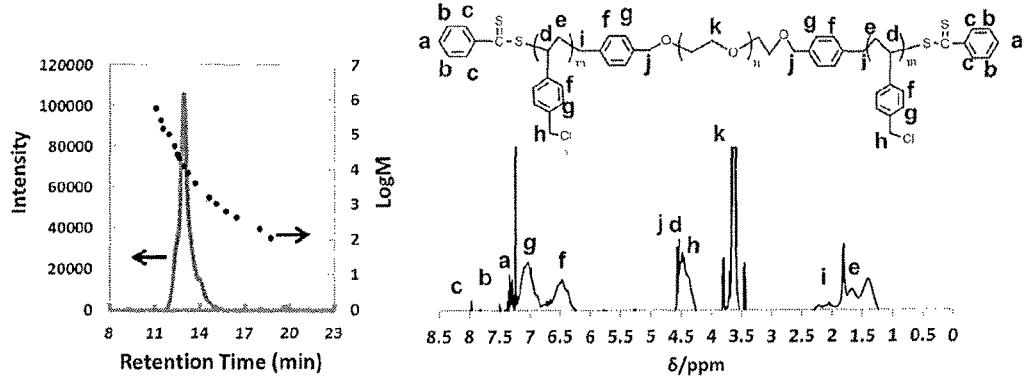

[FIG. 18]
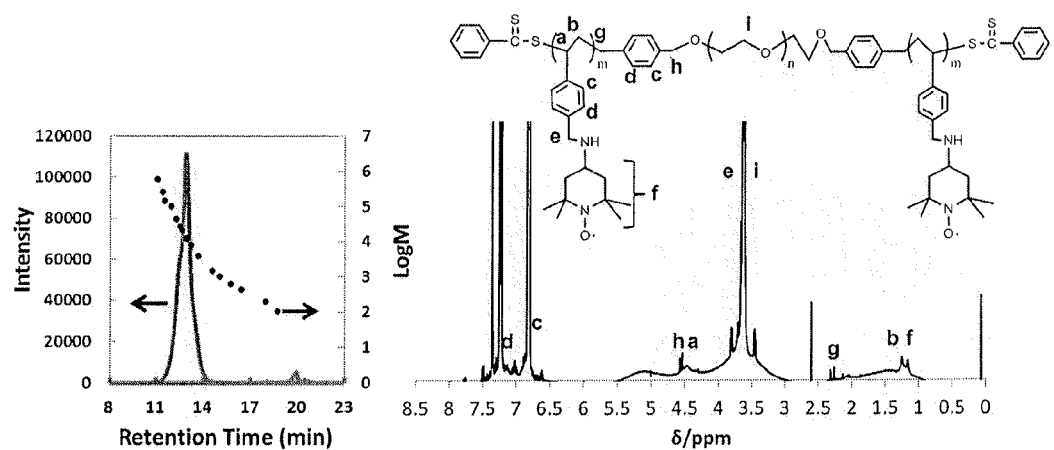
[FIG. 19]
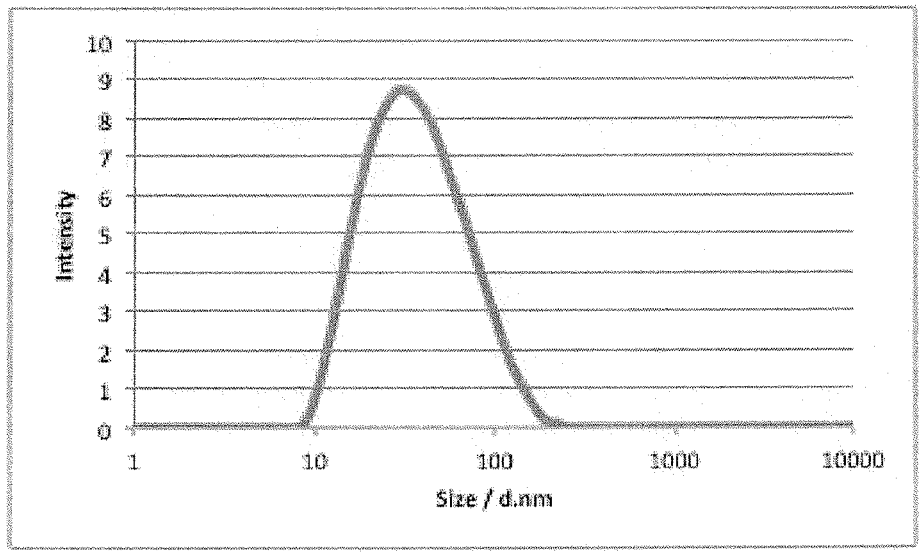

COMPOSITION CONTAINING POLYCATIONIC TRIBLOCK COPOLYMER, POLYANIONIC POLYMER AND PHYSIOLOGICALLY ACTIVE PEPTIDE

TECHNICAL FIELD

The present invention relates to a composition containing a polycationic triblock copolymer, a polyanionic polymer and a physiologically active peptide. More specifically, as, a result of the triblock copolymer being constituted from two polymer blocks each having, as a part of a pendant group, a cyclic nitroxide radical bonded via an amino group and a poly(ethylene glycol) block that is covalently bonded at both terminals to the two polymer blocks, the composition of the present invention can be provided as a polyion complex loaded with a physiologically active peptide or the like.

BACKGROUND ART

The present inventors et al. succeeded in forming a diblock polymer from a cyclic nitroxide radical compound, which encompasses 4-hydroxy-2,2,6,6-tetramethylpiperidin-1-oxyl or the like functioning as a radical scavenger for reactive oxygen species or the like, without adversely affecting the function of the compound, and filed a patent application for inventions relating to this diblock polymer per se and use of the diblock polymer in a certain technical field (see Patent Document 1). Furthermore, the present inventors et al. produced a so-called A-B-A type triblock copolymer in which two blocks (A) each having a cationically chargeable cyclic nitroxide radical as a pendant group are covalently bonded to both terminals of a poly(ethylene glycol) (PEG) chain (B). It has been confirmed and reported that such triblock copolymers form so-called flower micelles by using the formation of an ion complex with a polyanionic polymer in an aqueous medium as the driving force, that micelles formed in this way undergo gelation in response to biological environments, and that the thus formed gel exhibits high retainability in a local site and exhibits a high anti-inflammatory effect in inflammation models (for example, see Non-Patent Document 1, Non-Patent Document 2, Non-Patent Document 3 and Non-Patent Document 4, which are lecture proceedings for these reports).

Meanwhile, peptides and polypeptides, which encompass enzymes, proteins, and the like, have come to be used as drugs, and especially medical drugs, that utilize the specific reactivity, functionality or activity of such peptides and polypeptides. However, such peptides and polypeptides are decomposed by enzymes such as proteases in living bodies, which causes a variety of problems such as bioavailability of the peptides and polypeptides becoming extremely low and the occurrence of resistance and toxicity. In recent years, these problems have been solved by modification of poly (ethylene glycol), so called PEGylation of such substances, but many problems exist, such as a lowering of activity and reaction complexity. Attempts have been made to stabilize such substances by utilizing enzyme charging and complexing using polymers having the opposite charge (Non-Patent Document 5 and Non-Patent Document 6), but putting such methods to practical use have been impaired due to such complexes readily breaking down as a result of high ionic strength in living bodies. Furthermore, because polymers and the like are used in matrixes per se, the matrix is per se can cause inflammation, which is a problem.

PRIOR ART DOCUMENT

Patent Document

[Patent Document 1] WO2009/133647

Non-Patent Document

[Non-Patent Document 1] 2012.3.2 PB-13 Min Ley Pua, Pennapa Chonpathompiunlert, Toru Yoshitomi, Yukio Nagasaki, Novel redox flower micelle for chronic inflammation treatments, MANA International Symposium 2012, Tsukuba, Japan

[Non-Patent Document 2] 2012 6 7, Pua Min Ley, Pennapa Chonpathompiunlert, Toru Yoshitomi, Yukio Nagasaki, Development of Novel Nitroxide Radical-Containing Injectable Hydrogels for Treating Chronic Inflammation, 65th meeting of Society for Free Radical Research Japan, Tokushima, page 39

[Non-Patent Document 3] 2012.11.22 Pua Min Ley, Toru Yoshitomi, Pennapa Chonpathompiunlert, Aki Hirayama, and Yukio Nagasaki, "Redox Injectable Gel (RIG) for Treatments of Local Inflammation-Cattageenan-induced Arthritis-" International Workshop on Soft interface Science for Young Scientists (SIS YS 2012). Tsukuba, Japan

[Non-Patent Document 4] 2013.3.19-22 Pua Min Ley, Toru Yoshitomi, Pennapa Chonpathompiunlert, Aki Hirayama, and Yukio Nagasaki, Redox-active Injectable Gel (RIG) for Treatments of Carrageenan-Induced Arthritis, 2nd International Conference on Biomaterials Science in Tsukuba (ICBS2013), Tsukuba, Japan, P155

[Non-Patent Document 5] Atsushi Harada and Kazunori Kataoka (1998) "Novel Polyion Complex Micelles Entrapping Enzyme Molecules in the Core: Preparation of Narrowly-Distributed Micelles from Lysozyme and Poly (ethylene glycol)-Poly(aspartic acid) Block Copolymer in Aqueous Medium," Macromolecules 1998, 31, 288-294

[Non-Patent Document 6] Shin-ichi Sawada, Kazunari Akiyoshi (2010) "Nano-Encapsulation of Lipase by Self-Assembled Nanogels: Induction of High Enzyme Activity and Thermal Stabilization," Macromolecular Bioscience 2010, 10, 353-358

SUMMARY OF INVENTION

Here, it was found that physiologically active peptides, such as ampholytic proteins, generally maintain a charge balance in polyion complexes derived from triblock copolymers and polyanionic polymers in aqueous media while being able to be loaded in micelles formed from such polyion complexes and enabling gelation of such micelles in aqueous media. Furthermore, gels formed in this, way stably hold loaded physiologically active peptides in biological environments, but can enable release of peptides from gels into biological environments according to need.

Therefore, the present invention provides a composition that contains a triblock copolymer represented by formula (I), a polyanionic polymer and a physiologically active peptide or the like.

$$CNR\text{-}PEG\text{-}CNR \quad (I)$$

in the formula,

CNR moieties are each independently a polymer segment containing a repeating unit that contains, as a part of a pendant group, a cyclic nitroxide radical bonded to a main polymer chain via a linking group that contains at least one amino group (—NH—), unbonded terminals of the CNR moieties can each independently have, as a terminal group, a hydrogen atom, an arylthiocarbonylthio group, an alkylthiocarbonylthio group, an alkoxythiocarbonylthio group, a sulfanyl group, or the like, and PEG is a segment that contains poly(ethylene glycol).

A preferred aspect of the triblock copolymer is a copolymer represented by formula (II) below.

[Chemical Formula 1]

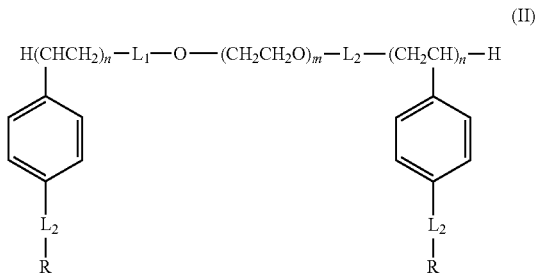

(II)

in the formula, the $L_1$ groups are linking groups that may be the same as, or different from, each other, the $L_2$ groups are each independently a —$C_{1-6}$ alkylene-NH—($C_{1-6}$ alkylene)q- group, with q being 0 or 1, the R groups are each independently such that at least 50% of the total number (n) of R groups are residues of cyclic nitroxide radical compounds selected from the group consisting of 2,2,6,6-tetramethylpiperidin-1-oxyl-4-yl groups, 2,2,5,5-tetramethylpyrrolidin-1-oxyl-3-yl groups, 2,2,5,5-tetramethylpyrrolin-1-oxyl-3-yl groups, 2,4,4-trimethyl-1,3-oxazolidin-3-oxyl-2-yl groups, 2,4,4-trimethyl-1,3-thiazolidin-3-oxyl-2-yl groups and 2,4,4-trimethyl-imidazolidin-3-oxyl-2-yl groups, with the remaining R groups, when present, being hydrogen atoms, halogen atoms or hydroxyl groups, the terminal H groups may, in some cases, each independently be substituted by arylthiocarbonylthio groups, alkylthiocarbonylthio groups, alkoxythiocarbonylthio groups, sulfanyl groups, and the like, m is an integer between 20 and 5,000, and each instance of n is independently an integer between 3 and 1,000.

In the composition, the blending quantities of the components are selected so that in an aqueous solution, the ratio of a total anionic charge relative to a total cationic charge from the triblock copolymer, the polyanionic polymer and the physiologically active peptide is between 1:10 and 10:1, preferably between 1:5 and 5:1, more preferably between 1:1.2 and 1.2:1, and particularly preferably 1:1.

In this way, the composition can be present as polyion complex micelles that exhibit fluidity in aqueous media, and these micelles can, for example, form stable gels in biological environments, with the gels being loaded with physiologically active peptides according to changes in ionic strength and/or changes in temperature. When placed at a desired location in a living body, the gels exhibit stability over a long period of time, but can release the loaded physiologically active peptide at the location in a controlled manner by exhibiting a balanced overall charge. Therefore, depending on the physiological activity of the loaded peptide in the medical field, the composition of the present invention can be used, for example, to treat disorders able to be prevented or treated by this activity.

DESCRIPTION OF THE INVENTION

In the present invention, the pendant group in the triblock copolymer means a side chain having a certain functional group, as is generally recognized in this technical field. Specifically, the pendant group is a group in which a cyclic nitroxide radical residue is covalently bonded to the right-hand terminal (as shown in the formula) of an o- or p-phenylene-($C_{1-6}$ alkylene-NH)p-($C_{1-6}$ alkylene)q-linking group (here, p is an integer between 1 and 3, and q is an integer of 0 or 1). More specifically, the pendant group in the present invention can be understood more clearly by referring to the side chain represented by -phenylene-($C_{1-6}$ alkylene-NH)p-($C_{1-6}$ alkylene)q-R in general formula (II) above. The main chain to which this type of pendent group is bonded is not particularly limited as long as the objective of the present invention is followed. In the present invention, "residue" means a group in a state whereby a hydrogen atom or 1 atom that constitutes another compound is removed from the compound in question, and in the case of a typical cyclic nitroxide radical, for example, it is possible to refer to the groups defined as R in general formula (II).

In this way, a preferred mode of the pendant group is one in which the cyclic nitroxide radical is bonded to the polymer main chain via an o- or p-phenylene-$C_{1-6}$ alkylene-NH—($C_{1-6}$ alkylene)q- (here, q is 0 or 1) linking group, and the cyclic nitroxide radical is selected from the group consisting of 2,2,6,6-tetramethylpiperidin-1-oxyl-4-yl, 2,2,5,5-tetramethylpyrrolidin-1-oxyl-3-yl, 2,2,5,5-tetramethylpyrrolin-1-oxyl-3-yl, 2,4,4-trimethyl-1,3-oxazolidine-3-oxyl-2-yl, 2,4,4-trimethyl-1,3-thiazolidin-3-oxyl-2-yl and 2,4,4-trimethyl-imidazolidin-3-oxyl-2-yl.

In a triblock copolymer or polycation thereof, which is characterized in that the main chain is bonded to the unbonded phenylene terminal (the opposite terminal from the terminal having the cyclic nitroxide radical via an amino (—NH—) group), "the unbonded phenylene terminal" means the terminal on the opposite side from the position at which the $C_{1-6}$ alkylene of the o- or p-phenylene is bonded. In addition, in the description of the present application, bonding means covalent bonding unless otherwise specified.

The polymer main chain is not particularly limited as long as the objective of the present invention is followed, as mentioned above, but is preferably a main chain having a polymerizable unsaturated double bond, for example, a main chain formed by radical polymerization of a polymerizable monomer having an unsaturated double bond, such as a substituted ethylene. Specific examples of such main chains include those disclosed in Patent Document 1.

A more preferred triblock copolymer is that represented by formula (II), which is given above as an example of a preferred aspect.

In formula (II), the linking groups defined as $L_1$ are preferably each independently selected from the group consisting of single bonds, —S—$(CH_2)_c$— groups, —S—$(CH_2)_c$CO— groups, —$(CH_2)_c$S— groups, —CO$(CH_2)_c$S— groups, m- or p-phenylene groups, m- or p-xylylene groups, alkylene groups and the like, c can be an integer between 1 and 5, with these linking groups able to be in the opposite direction from that shown in formula (II) in cases where the linking groups are not directionally equivalent, the R groups are each independently such that at least 50%, preferably at least 80%, more preferably at least 90%, and further preferably approximately 100%, of the total number (n) of R groups are residues of cyclic nitroxide radical compounds selected from the group consisting, of 2,2,6,6-tetramethylpiperidin-1-oxyl-4-yl groups, 2,2,5,5-tetramethylpyrrolidin-1-oxyl-3-yl groups, 2,2,5,5-tetramethylpyrrolin-1-oxyl-3-yl groups, 2,4,4-trimethyl-1,3-oxazolidin-3-oxyl-2-yl groups, 2,4,4-trimethyl-1,3-thiazolidin-3-oxyl-2-yl groups and 2,4,4-trimethyl-imidazolidin-3-oxyl-2-yl groups, with the remaining R groups, when present, being hydrogen atoms, halogen atoms or hydroxyl groups, m is an integer between 20 and 5,000, preferably between 20 and 1,000, and more preferably between 50 and 200, and each instance of n is independently an integer between 3 and 1,000, preferably between 3 and 100, and more preferably between 3 and 50.

The $C_{1-6}$ alkylene group is not limited, and specific examples thereof include diyl groups of corresponding alkyl groups, such as methylene groups, 1,2-propane diyl groups, 1,3-propane diyl groups and 1,4-butane diyl groups.

The cyclic nitroxide radical of the R group is preferably a group represented by the following formula:

[Chemical Formula 2]

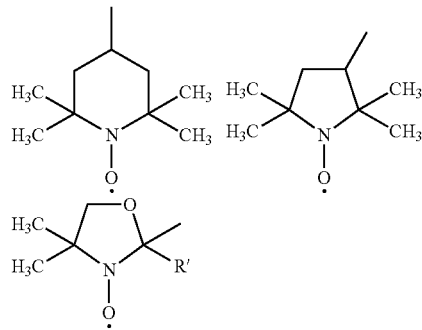

in the formula, R' is a methyl group.

Among the groups listed above, the residue represented by the first formula is a group that is referred to as TEMPO hereinafter.

This type of triblock copolymer can be advantageously produced by preparing a precursor of the triblock copolymer having the main chain or the main chain and a part of the pendant group, and then introducing a cyclic nitroxide radical residue into the precursor. In another method, each block is prepared independently and these blocks are then covalently bonded to each other so as to form the target triblock copolymer. Typical production methods are shown in the working examples explained later, but it is possible to bond a polymer segment able to form a CNR precursor to a terminal of a poly(ethylene glycol) that is modified so as to be reactive at both terminals, grow the polymer chain from both terminals, and then introduce a cyclic nitroxide radical that is bonded via a linking group having at least 1 amino group. Specific examples can be seen in Non-Patent Documents 2 and 4, but more specifically, it is possible to refer to the method disclosed in the international patent application PCT/JP2013/051395, which was filed by the present inventors et al. The contents of that application are incorporated by reference in the contents of the present specification.

The polyanionic polymer used in the present invention can be poly(acrylic acid), poly(methacrylic acid), poly(sulfonic acid), a polyanionic polysaccharide (for example, carboxymethyl dextran, carrageenan, xanthan gum, short chain degradation fragments thereof, and the like), an anionic protein (for example, albumin, poly(aspartic acid), poly(glutamic acid)), or the like, and the optimal molecular weights of these polyanionic polymers vary according to the type of polymer and are not particularly limited, but in the case of poly(acrylic acid), for example, the Mn value is 1,000-1,000,000, preferably 1,000-100,000, and more preferably 1,000-10,000. These can be commercially available products in an unmodified state or products that have been refined according to need.

In the present invention, the physiologically active peptide or the like may be any compound or substance able to be loaded into, or encapsulated by, micelles of a polyion complex (PIC) formed from the composition of the present invention or a gel formed from the composition or the micelles, and thereby able to be stabilized in, for example, aqueous media, aqueous solutions and aqueous environments, which are of technical significance. In the present invention, the terms "peptide" and "peptide or the like" are general terms that encompass low molecular weight peptides, oligopeptides and polypeptides, and polypeptides encompass a variety of proteins. Such proteins can encompass glycoproteins and lipoproteins that are modified by sugars or lipids. Therefore, the physiologically active peptide is not limited, but can be an enzyme protein, such as an oxidase (for example, an amino acid-oxidizing enzyme), a lipase, urokinase, a lysozyme or trypsin, an antigenic protein used as a raw material for a medical vaccine, such as MAGE-A4, an antibody having anti-cancer activity (including antibody fragments and single-chain antibodies (scFv)), such as folate receptor 4, an antibody such as HER2-targeting IgG1κ or EGFR-targeting IgG2κ, a cytokine or growth factor such as interferon α, interferon β, interleukin, TNF-α, TNF-β, a bone-forming protein (BMP-11 or the like) or a growth differentiation factor (GDF-11 or the like), a peptide hormone such as insulin, calcitonin, a thyroid stimulating hormone-releasing hormone (for example, thyroliberin), a luteinizing hormone-releasing hormone (for example, somatotropin), an adreno-corticotrophic hormone, an adreno-corticotrophic hormone-releasing hormone, a growth hormone releasing factor, a gonadotrophic hormone, a gonadotrophic hormone-releasing hormone, angiotensin, gastrin, a melanocyte-stimulating hormone, β-endorphin, erythropoietin, urogastrone, a growth hormone release-inhibiting hormone or an atrial natriuretic peptide, or an antimicrobial peptide such as lactoferricin, a bacteriocin or nisin. These peptides may be naturally derived, may be produced using gene recombination techniques, and may be obtained through glycosylation by, for example, post-translational modification of peptides (or polypeptides) produced using such peptide synthesis techniques.

As mentioned above, in the composition of the present invention, the blending quantities of the components are selected so that in an aqueous solution, the ratio of the total anionic charge relative to the total cationic charge from the triblock copolymer, the polyanionic polymer, the physiologically active peptide and the like is between 1:10 and 10:1, preferably between 1:5 and 5:1, more preferably between 1:1.2 and 1.2:1, and particularly preferably 1:1. When deciding such blending quantities, the blending quantity of the physiologically active peptide, such as an ampholytic protein, is decided by adjusting the blending quantity of the triblock copolymer or the polyanionic polymer in view of the isoelectric points (pI) thereof so that the charge of the overall composition is balanced at a certain pH. In the present invention, the aqueous medium, aqueous solution or aqueous environment may be water, deionized water or sterilized water, but may contain a non-toxic buffering agent, and may be a bodily fluid of a warm-blooded animal (or preferably human) or an organ or tissue that contains such a bodily fluid.

The composition of the present invention contains a simple mixture of the 3 components mentioned above, but preferably contains these components at quantities whereby the charge of the overall composition is balanced, as mentioned above. In this way, the composition forms micelles due to these molecules associating in an aqueous solution, and the composition is present as transparent PIC micelles, as if the composition were dissolved. When measured by a dynamic light scattering (DLS) method, such PIC micelles have an average particle diameter of between several tens of nanometers and several hundred nanometers, preferably 10 nm to 300 nm, more preferably 20 nm to 200 nm, and most preferably 30 nm to 150 nm. Therefore, in cases where the composition of the present invention is used as, for example, a medicine, the medicine can be easily administered by injection, physical inflammation that occurs upon gel formation can be suppressed by nitroxy radicals bonded to the triblock copolymer, the triblock copolymer to which the nitroxy radicals are bonded does not penetrate into cells following degradation of the gel, and the composition of the present invention can therefore be used advantageously by preventing adverse reactions without obstructing electron transport system in cells.

This type of micelle solution forms a stable gel according to changes in the ionic strength in the aqueous solution and/or changes in temperature. In general, ionic strength can be adjusted by means of a substance able to be ionized in an aqueous solution. By altering the final ionic concentration of an ionizable substance, which is added to the micelle solution at room temperature, in the micelle solution from 0 to 50 mM (and preferably 0 mM) to an ionic concentration of 150 mM or higher, the micelle solution can form a gel. With regard to the temperature, the composition of the present invention is such that the micelles are generally formed in the aqueous solution at room temperature, but by increasing the temperature to approximately 37° C. or higher, the micelle solution forms a gel. This type of gelation can be brought about by simultaneously altering the ionic concentration and the temperature. The ionizable substance is an inorganic salt and is not particularly limited, but examples thereof include sodium chloride, potassium chloride, sodium bromide, potassium bromide, sodium sulfate, sodium dihydrogen phosphate and disodium hydrogen phosphate.

In addition, the PIC formed from the composition of the present invention can be provided as a gel-forming composition that contains a physiologically acceptable diluent or excipient. This type of diluent can be sterilized water, a mineral acid-containing acidic aqueous solution, a physiological saline solution, a weakly acidic or weakly alkaline solution containing a physiologically acceptable buffering agent, or the like. The excipient can be, for example, sorbitol, dextrin, glucose, mannitol, an amino acid (glycine, isoleucine, valine, methionine, glutamic acid, or the like), or the like.

Furthermore, by administering this composition to patients for whom the use of a physiologically active peptide or the like is essential and suppression of inflammation is desirable (by a means such as intravenous, intraarterial, subcutaneous or intramuscular administration in the case of a micelle solution) or by directly injecting the composition into a lesion, and then gelating the composition, the obtained gel remains at the site of injection for a long period of time and slowly releases the physiologically active peptide or the like according to need, thereby making it possible to treat a condition or disorder that requires treatment using the physiologically active peptide.

BRIEF DESCRIPTION OF DRAWINGS

FIG. 1 is a diagram showing the results of size exclusion chromatography (SEC) measurements and $^1$H NMR spectral measurements for the PCMS-b-PEG-b-PCMS triblock copolymer obtained in Production Example 1.

FIG. 2 is a diagram showing the results of SEC measurements and $^1$H NMR spectral measurements for the PMNT-b-PEG-b-PMNT triblock copolymer obtained in Production Example 2.

FIG. 3 shows photographs relating to diagrams showing the state of gelation of the polyion complex micelles prepared in Production Example 4.

FIG. 4 indicates the results of Experiment 1, and is a diagram showing the hydrogen peroxide production capacity of a polyion complex that encapsulates D-amino acid oxidase.

FIG. 5 is a diagram showing particle diameter measurement results for the protein-encapsulating PIC micelles obtained in Production Examples 5 to 7 and the PIC micelles obtained in Comparative Example 1. In this diagram, ◊ relate to FITC-Insulin-encapsulating PIC micelles, □ relate to FITC-BSA-encapsulating PIC micelles, and ▲ relates to FITC-GOD-encapsulating PIC micelles. ● relates to PIC micelles that contain no protein.

FIG. 6 shows the results of fluorescence intensity measurements for a FITC-Insulin-encapsulating PIC micelle solution and a FITC-Insulin aqueous solution in a FITC-Insulin solution, for the same protein concentration.

FIG. 7 shows the results of fluorescence intensity measurements for a FITC-BSA-encapsulating PIC micelle solution and a FITC-BSA aqueous solution in a FITC-BSA solution, for the same protein concentration.

FIG. 8 shows the results of fluorescence intensity measurements for a FITC-GOD-encapsulating PIC micelle solution and a FITC-GOD aqueous solution in a FITC-GOD solution, for the same protein concentration.

FIG. 9 shows the results of protein release measurements from RIG in Experimental Example 2. ● relate to FITC-Insulin-encapsulating RIG, ■ relate to FITC-BSA-encapsulating RIG, and Δ relate to FITC-GOD-encapsulating RIG.

FIG. 10 shows photographs that indicate the results of an in vivo protein release evaluation test from RIG in Experimental Example 3.

FIG. 11 shows photographs that indicate the results of a RIG in vivo retention evaluation test in Experimental Example 3.

FIG. 12 shows photographs that indicate the results of a protein in vivo retention evaluation test in Experimental Example 4.

FIG. 13 shows gelation behavior according to changes in the temperature and ionic strength of a (DAO-containing) PIC micelle solution in Experimental Example 5.

FIG. 14 shows gelation behavior according to changes in the temperature and ionic strength of a (DAO-free) PIC micelle solution in Experimental Example 5.

FIG. 15 is a diagram showing the results of SEC measurements and $^1$H NMR spectral measurements for the Br-PEG-Br obtained in Production Example 14.

FIG. 16 is a diagram showing the results of SEC measurements and $^1$H NMR spectral measurements for the CTA-PEG-CTA obtained in Production Example 15.

FIG. 17 is a diagram showing the results of SEC measurements and $^1$H NMR spectral measurements for the PCMS-b-PEG-b-PCMS triblock copolymer obtained in Production Example 16.

FIG. 18 is a diagram showing the results of SEC measurements and ¹H NMR spectral measurements for the PMNT-b-PEG-b-PMNT triblock copolymer obtained in Production Example 17.

FIG. 19 is a diagram showing particle diameter measurement results for the polyion complex micelles obtained in Production Example 18.

EXAMPLES

The present invention will now be explained in greater detail through the use of specific examples, but the present invention is in no way limited to these specific examples.

<Production Example 1> Synthesis of Polychloromethylstyrene-b-Poly(Ethylene Glycol)-b-Polychloromethylstyrene (PCMS-b-PEG-b-PCMS) Triblock Copolymer The PCMS-b-PEG-b-PCMS was synthesized according to Synthesis Scheme 1 shown below:

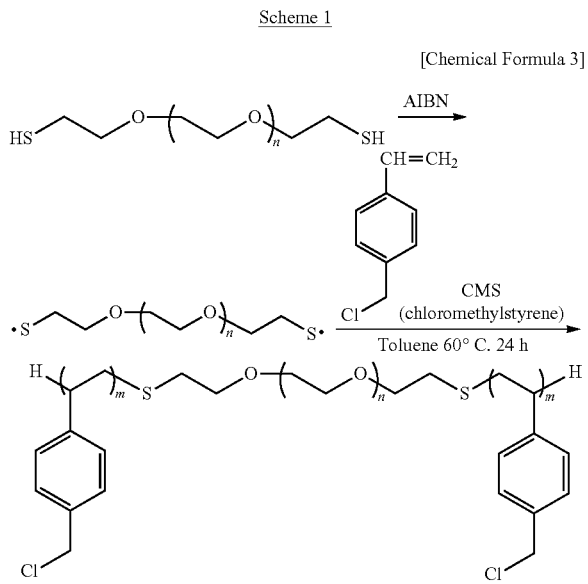

Poly(ethylene glycol) having a thiol group at both terminals (HS-PEG-SH) (Mn: 10,000; 0.164 mmol, 1.64 g) was added to a reaction vessel. Next, a procedure involving evacuating the reaction vessel to a vacuum and blowing in nitrogen gas was repeated 3 times so as to form a nitrogen atmosphere in the reaction vessel. A solution of azobisisobutyronitrile/toluene (0.164 mmol/16 ml) and a solution of chloromethylstyrene (12.3 mmol, 1.74 mL) were added to the reaction vessel, heated to 60° C. and stirred for 24 hours. A white powder was obtained by washing the reaction mixture 3 times with diethyl ether, which is a good solvent for a polychloromethylstyrene homopolymer, and then freeze-drying in benzene. The quantity recovered was 2.07 mg, which was a yield of 96.5%. The results of size exclusion chromatography (SEC) measurements and ¹H NMR spectral measurements for the obtained PCMS-b-PEG-b-PCMS triblock copolymer are shown in FIG. 1.

<Production Example 2> Synthesis of Triblock Polymer Containing 2,2,6,6-tetramethylpiperidin-1-oxyl-4-yl (TEMPO) (PMNT-b-PEG-b-PMNT)

PCMS-b-PEG-b-PCMS (Mn: 13,052; 1.8 g, 0.138 mmol) was added to a reaction vessel. Next, 4-amino-TEMPO (2.36 g, 13.8 mmol) was dissolved in 20 mL of dimethyl sulfoxide (DMSO), added to the reaction vessel, and stirred for 24 hours at room temperature. Following completion of the reaction, the reaction solution was added to a dialysis membrane (Spectra/Por molecular weight cut-off size 3,500 Spectrum Medical Industries Inc., Houston Tex.), and dialyzed with 2 L of methanol. The methanol was replaced 8 times, every 2 hours, after which the reaction solution was evaporated and freeze-dried in benzene. The yield was 65.6%.

It was found from ¹H NMR measurements that 100% of the chloromethyl groups had reacted and TEMPO had been introduced (see FIG. 2).

<Production Example 3> Design of Polyion Complex Micelles

The powdered PMNT-b-PEG-b-PMNT triblock polymer was dissolved in a 0.1 M aqueous solution of HCl, the amino groups on the PMNT chains were completely protonated, and the aqueous system was freeze-dried and recovered. Next, the PMNT-b-PEG-b-PMNT triblock polymer and poly (acrylic acid) (PAA; Mn: 5,000) were each dissolved in a phosphoric acid buffer solution (0.1 M, pH 6.28) so as to prepare an aqueous polycationic PMNT-b-PEG-b-PMNT solution and an aqueous anionic PAA solution, each having a concentration of 5 mg/ml. In addition, D-amino acid oxidase was dissolved in a phosphoric acid buffer solution (0.1 M, pH 6.28), thereby adjusting the concentration to 0.2 mg/ml. The D-amino acid oxidase was added to the aqueous PAA solution under stirring. PIC micelles were then produced by adding the aqueous PMNT-b-PEG-b-PMNT triblock polymer solution dropwise under stirring to the mixed solution containing the PAA and the D-amino acid oxidase. Here, the PIC micelles were produced in such a way that the PMNT-b-PEG-b-PMNT:PAA molar ratio (r) was 1:1, under conditions whereby the quantity of DAO was changed to 0 ml, 0.2 ml, 0.4 ml or 0.6 ml. (Molar ratio (r)=[number of moles of activated carboxyl groups in PAA]/[number of moles of activated amino groups in PMNT-b-PEG-b-PMNT]). The zeta potential of the obtained PIC micelles was measured. The results are shown in Table 1. When the average particle diameter of the obtained PIC micelles was measured by dynamic light scattering (DLS), it was confirmed that the PIC micelles were unimodal particles having an average particle diameter of 59-67 nm.

TABLE 1

Particle diameter and zeta potential of polyion complex micelles

| | DAO (0.2 mg/ml) | Particle diameter | PDI (polydispersity index) | z-potential |
|---|---|---|---|---|
| (1) | 0 ml | 66.7 nm | 0.258 | +1.22 |
| (2) | 0.2 ml | 63.0 nm | 0.251 | +0.654 |
| (3) | 0.4 ml | 66.6 nm | 0.251 | +1.54 |
| (4) | 0.6 ml | 59.5 nm | 0.241 | +0.395 |

<Production Example 4> Design of Injectable Gel 5 mg/ml of each PIC micelle solution prepared in Production Example 3 was condensed by centrifugal evaporation, thereby adjusting the ionic strength to 150 mM, and gelation experiments were carried out in a water bath at a temperature of 37° C. using a test tube inversion method. Photographs relating to diagrams showing the experimental results (the state of gelation) are shown in FIG. 3. From these diagrams, it was confirmed that an irreversible gel was formed at an ionic strength of 150 mM and a temperature of 37° C.

<Experimental Example 1> Evaluation of Hydrogen Peroxide Production Capacity of D-Amino Acid Oxidase PIC micelles to which 0.4 ml (0.2 mg/ml) of D-amino acid oxidase was added ((3) in table 1 and FIG. 3) were evaluated in terms of hydrogen peroxide production capacity using a peroxidase/o-dianisidine evaluation method. The D-amino acid oxidase was condensed by centrifugal evaporation until the concentration was 5 µg/ml, and evaluated through a comparison with control PIC micelles in which the amount of free DAO and D-amino acid oxidase was 0 ml. The results are shown in FIG. 4.

This diagram shows that free D-amino acid oxidase and D-amino acid oxidase-encapsulating PIC micelles exhibit different behavior in terms of hydrogen peroxide production capacity. This is thought to be because the D-amino acid oxidase is incorporated into the PIC micelles through electrostatic interactions. In addition, it can be understood that PIC micelles in which D-amino acid oxidase is encapsulated or loaded slowly release hydrogen peroxide, and are therefore materials that can prevent an initial burst of a drug.

Production Examples 5 to 7

Preparation of PIC Micelles Encapsulating Fluorescein Isothiocyanate (FITC)-Labeled Proteins The powdered PMNT-b-PEG-b-PMNT triblock polymer was dissolved in a 0.1 M aqueous solution of HCl, the amino groups on the PMNT chains were completely protonated, and the aqueous system was freeze-dried and recovered.

Next, the protonated PMNT-b-PEG-b-PMNT triblock polymer and poly(acrylic acid) (PAA; Mn: 5,000) were each dissolved in a phosphoric acid buffer solution (50 mM, pH 6.2), thereby preparing a polycationic PMNT-b-PEG-b-PMNT aqueous solution and a polyanionic PAA aqueous solution each having a concentration of 5 mg/ml.

To 1.621 mL of the aqueous PAA solution prepared in the manner described above, the following materials were added:
  i) 70 µL of an aqueous solution obtained by dissolving 1492 µg/mL of fluorescein isothiocyanate-labeled insulin (FITC-Insulin) in a phosphate-buffered physiological saline solution (PBS),
  ii) 51 µL of an aqueous solution obtained by dissolving 2030 µg/mL of FITC-labeled bovine serum albumin (FITC-BSA) in a phosphoric acid buffer solution (50 mM, pH 6.2), or
    iii) 63 µL of an aqueous solution obtained by dissolving 1650 µg/mL of FITC-labeled glucose oxidase (FITC-GOD) in a phosphate-buffered physiological saline solution (PBS) and stirred. Next, 10 mL of the aqueous solution of the PMNT-b-PEG-b-PMNT triblock polymer was added dropwise under stirring to the mixed solutions of PAA and FITC-proteins under ice cooling, 309 µL, 328 µL and 316 µL respectively of a phosphoric acid buffer solution (50 mM, pH 6.2) was added, thereby preparing PIC micelles encapsulating FITC-Insulin, FITC-BSA and FITC-GOD respectively.

Here, the PIC micelles were prepared so that the PMNT-b-PEG-b-PMNT:PAA molar ratio (r) was 1:1 (molar ratio (r)=[number of moles of activated carboxyl groups in PAA]/ [number of moles of activated amino groups in PMNT-b-PEG-b-PMNT]).

The particle diameters of the obtained FITC-protein-encapsulating PIC micelles, as measured by dynamic light scattering (DLS), are shown in FIG. 5 and Table 2.

TABLE 2

Average particle diameters and polydispersity indices of protein-encapsulating PIC micelles and PIC micelles (PdI)

|  | Average particle diameter (nm) | PdI |
|---|---|---|
| FITC-Insulin-encapsulating PIC micelles | 66.01 | 0.261 |
| FITC-BSA-encapsulating PIC micelles | 56.34 | 0.239 |
| FITC-GOD-encapsulating PIC micelles | 62.19 | 0.247 |
| PIC micelles | 42.95 | 0.172 |

The results of fluorescence intensity measurements of the obtained FITC-Insulin-encapsulating PIC micelle solution, FITC-BSA-encapsulating PIC micelle solution and FITC-GOD-encapsulating PIC micelle solution are shown in FIGS. 6, 7 and 8. In addition, the FITC-protein concentration in each FITC-protein-encapsulating PIC micelle solution and the fluorescence intensities of the FITC-protein aqueous solutions at the same concentrations are also shown in FIGS. 6, 7 and 8. Quenching caused by fluorescence resonance energy transfer (FRET) was confirmed in each FITC-protein-encapsulating PIC micelle solution, which suggested that insulin, bovine serum albumin and glucose oxidase were encapsulated in the PIC micelles.

<Reference Example 1> Preparation of PIC Micelles not Encapsulating Proteins

The powdered PMNT-b-PEG-b-PMNT triblock polymer was dissolved in a 0.1 M aqueous solution of HCl, the amino groups on the PMNT chains were completely protonated, and the aqueous system was freeze-dried and recovered.

Next, the protonated PMNT-b-PEG-b-PMNT triblock polymer and poly(acrylic acid) (PAA; Mn: 5,000) where each dissolved in a phosphoric acid buffer solution (50 mM, pH 6.2), thereby preparing a polycationic PMNT-b-PEG-b-PMNT aqueous solution and a polyanionic PAA aqueous solution each having a concentration of 5 mg/ml.

PIC micelles were prepared by adding 10 mL of an aqueous solution of the PMNT-b-PEG-b-PMNT triblock polymer dropwise under stirring and under ice cooling to 1.621 mL of the aqueous PAA solution prepared in the manner described above. Here, the PIC micelles were prepared so that the PMNT-b-PEG-b-PMNT:PAA molar ratio (r) was 1:1 (the molar ratio (r) is as defined above). The particle diameters of the obtained PIC micelles, as measured by dynamic light scattering (DLS), are shown in FIG. 5 and Table 2.

<Production Examples 8 to 10> Preparation of FITC-Protein-Encapsulating Redox Injectable Gels (RIG)

11 mL of each of the FITC-protein-encapsulating PIC micelle solutions obtained in Production Examples 5 to 7 were condensed to 1 mL by means of centrifugal evaporation. A FITC-Insulin-encapsulating RIG, a FITC-BSA-encapsulating RIG and a FITC-GOD-encapsulating RIG were prepared by placing 300 µL of each of the condensed solutions in a 1.5 mL microtube and heating in a constant temperature bath at a temperature of 37° C.

<Experimental Example 2> Evaluation of Release of Proteins from Redox Injectable Gels (RIG)

150 µL of PBS was added to microtubes containing the protein-encapsulating RIGs obtained in Production Examples 8 to 10, and the obtained mixtures were incubated at 37° C. and 100 rpm using a shaker. At the sampling point, 100 µL of the supernatant liquid was extracted and 100 µL of fresh PBS was added. The fluorescence intensity of the extracted supernatant liquid was measured using a plate reader, and the quantity of protein released was calculated from the fluorescence intensity. These results are shown in FIG. 9.

<Production Example 11> Preparation of HiLyte Fluor 647-Labeled PIC Micelles Encapsulating Indocyanine Green (ICG)-Labeled Bovine Serum Albumin (BSA)

The powdered PMNT-b-PEG-b-PMNT triblock polymer was dissolved in a 0.1 M aqueous solution of HCl, the amino groups on the PMNT chains were completely protonated, and the aqueous system was freeze-dried and recovered.

Next, the protonated PMNT-b-PEG-b-PMNT triblock polymer and poly(acrylic acid) (PAA; Mn: 5,000) where each dissolved in a phosphoric acid buffer solution (50 mM, pH 6.2), thereby preparing a polycationic PMNT-b-PEG-b-PMNT aqueous solution and a polyanionic PAA aqueous solution each having a concentration of 5 mg/ml.

205 µL of an aqueous solution obtained by dissolving 1000 µg/ml of indocyanine green (ICG)-labeled bovine serum albumin (ICG-BSA) in a phosphate buffered physiological saline solution (PBS) was added under stirring to 2.76 mL of the aqueous PAA solution prepared in the manner described above. Next, ICG-BSA-encapsulating HiLyte Fluor 647-PIC micelles were prepared by adding a mixed solution consisting of 10 mL of an aqueous solution of the PMNT-b-PEG-b-PMNT triblock polymer and 0.3 mL of an aqueous solution obtained by dissolving 1.67 mg/mL of the HiLyte Fluor 647-labeled PMNT-b-PEG-b-PMNT triblock polymer in a phosphoric acid buffer solution (50 mM, pH 6.2) dropwise under stirring and under ice cooling to the next solution of PAA and ICG-BSA, and then adding 335 µL of a phosphoric acid buffer solution (50 mM, pH 6.2). Here, the PIC micelles were prepared so that the PMNT-b-PEG-b-PMNT PAA molar ratio (r) was 1:1 (the molar ratio (r) is as defined above).

<Experimental Example 3> Evaluation of In Vivo Release of Proteins from Redox Injectable Gels (RIG) and Evaluation of In Vivo Retention of RIGs 22 mL of the ICG-BSA-encapsulating HiLyte Fluor 647-PIC micelle solution obtained in Production. Example 11 was condensed to 2 mL by centrifugal evaporation. 200 µL of the condensed solution was subcutaneously injected into BALB/c-nu mice. The release of BSA from RIGs and RIG retention were evaluated by imaging a labeled fluorescent dye using an IVIS Spectrum. A fluorescence filter having an excitation wavelength of 745 nm and a fluorescence wavelength of 800 nm was used when imaging ICG-BSA, and a fluorescence filter having an excitation wavelength of 640 nm and a fluorescence wavelength of 680 nm was used when imaging HiLyte Fluor 647-RIG. The results are shown in FIGS. 10 and 11. It was confirmed that RIG-encapsulated BSA remained at the administration site for 14 days and was slowly released. In addition, it was confirmed that the RIG remained at the administration site for 1 month or longer.

<Experimental Example 4> Evaluation of In Vivo Retention of Proteins

200 µL of an aqueous solution obtained by dissolving 100 µg/mL of ICG-BSA in a phosphate-buffered physiological saline solution (PBS) was subcutaneously injected into BALB/c-nu mice. BSA Retention was evaluated by imaging a labeled fluorescent dye (ICG) using an IVIS Spectrum. The imaging was carried out using a fluorescent filter having an excitation wavelength of 745 nm and a fluorescence wavelength of 800 nm. The results are shown in FIG. 12. It was confirmed that in cases where BSA was administered in isolation, the BSA disappeared from the administration site after 1 day.

<Production Example 12> Preparation of D-Amino Acid Oxidase (DAO)-Encapsulating PIC Micelles The powdered PMNT-b-PEG-b-PMNT triblock polymer was dissolved in a 0.1 M aqueous solution of HCl, the amino groups on the PMNT chains were completely protonated, and the aqueous system was freeze-dried and recovered.

Next, the protonated PMNT-b-PEG-b-PMNT triblock polymer and poly(acrylic acid) (PAA; Mn: 5,000) were each dissolved in a phosphoric acid buffer solution (100 mM, pH 6.2), thereby preparing a polycationic PMNT-b-PEG-b-PMNT aqueous solution and a polyanionic PAA aqueous solution each having a concentration of 5 mg/ml.

347 µL of an aqueous solution obtained by dissolving 1 mg/mL of D-amino acid oxidase (DAO) in a phosphoric acid buffer solution (100 mM, pH 6.2) was added under stirring to 2.76 mL of the aqueous PAA solution prepared in the manner described above. Next D-amino acid oxidase (DAO)-encapsulating PIC micelles were prepared by adding 20 mL of an aqueous solution of the PMNT-b-PEG-b-PMNT triblock polymer dropwise under stirring and under ice cooling to a mixed solution of PAA and the D-amino acid oxidase (DAO). Here, the PIC micelles were prepared so that the PMNT-b-PEG-b-PMNT:PAA molar ratio (r) was 1:1 (molar ratio (r)=[number of moles of activated carboxyl groups in PAA]/[number of moles of activated amino groups in PMNT-b-PEG-b-PMNT]).

<Production Example 13> Preparation of D-Amino Acid Oxidase (DAO)-Encapsulatingredox Injectable Gel (RIG)

10 mL of the encapsulating PIC micelle solution obtained in Production Example 12 was condensed to 1.5 mL by centrifugal evaporation. 300 µl of the condensed solution was diluted to 502.5 µl by adding aqueous NaCl solutions having different concentrations, and DAO (D-amino acid oxidase)-encapsulating PIC micelle solutions were prepared, so as to have NaCl concentrations of 0 mM, 150 mM, 300 mM, 500 mM and 1000 mM and PIC concentrations of 20 mg/ml.

<Experimental Example 5> Gelation Behavior Caused by Changes in Ionic Strength

The D-amino acid oxidase (DAO)-encapsulating RIG produced in Production Example 13 was placed in a 300 µl cell, the transmittance at 600 nm was measured using a UV-VIS apparatus, and gelation was observed when the temperature was gradually increased. The results are shown in FIG. 13. It was confirmed that gelation was facilitated as the ionic strength increased. In addition, with regard to a DAO-free PIC micelle solution, D-amino acid oxidase (DAO)-free PIC micelles (corresponding to a system in which the D-amino acid oxidase of Production Example 12 is not added) were prepared in the same way as the PIC micelles and preparation example described in Production Example 12, and the gelation behavior caused by changes in the ionic strength of the micelle solution was evaluated using the method of Production Example 13. The results of transmittance measurements obtained by altering the temperature and salt concentration are shown in FIG. 14.

<Production Example 14> Synthesis of Br-PEG(Poly(Ethylene Glycol))-Br

The Br-PEG-Br was synthesized according to Synthesis Scheme 2 shown below:

Scheme 2

[Chemical Formula 4]

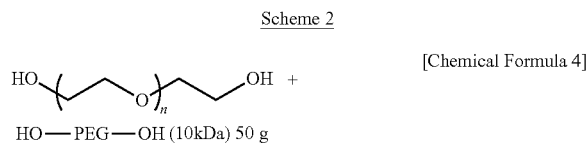

HO—PEG—OH (10kDa) 50 g

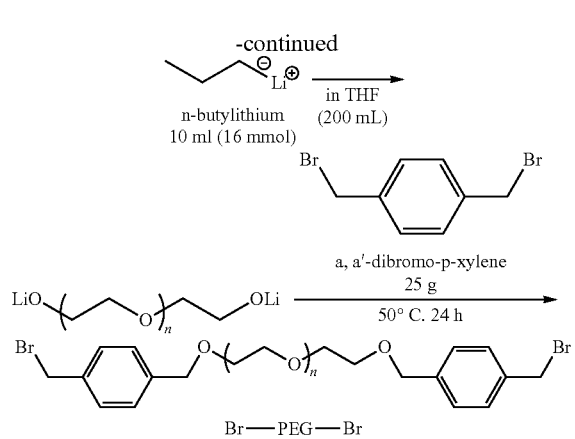

A poly(ethylene glycol) having a hydroxyl group at both terminals (OH-PEG-OH) (Mn: 10,000; 50 g) was dehydrated by means of vacuum drying at 110° C. for 12 hours. Next, 200 ml of THF was added, 10 ml (16 mmol) of butyl lithium and 25 g of dibromoxylene were added thereto, and a reaction was allowed to progress at 50° C. for 24 hours, thereby obtaining Br-PEG-Br, which was brominated at both terminals. The obtained polymer was purified by being precipitated in 2-propanol and vacuum dried. The results of size exclusion chromatography (SEC) measurements and $^1$H-NMR spectral measurements for the obtained Br-PEG-Br are shown in FIG. 15.

<Production Example 15> Synthesis of CTA (Chain Transfer Agent)-PEG-CTA (Chain Transfer Agent) (Synthesis of PEG Having a Dithiophenyl Ester at Both Terminals)

The CTA-PEG-CTA was synthesized according to Synthesis Scheme 3 shown below:

Scheme 3

[Chemical Formula 5]

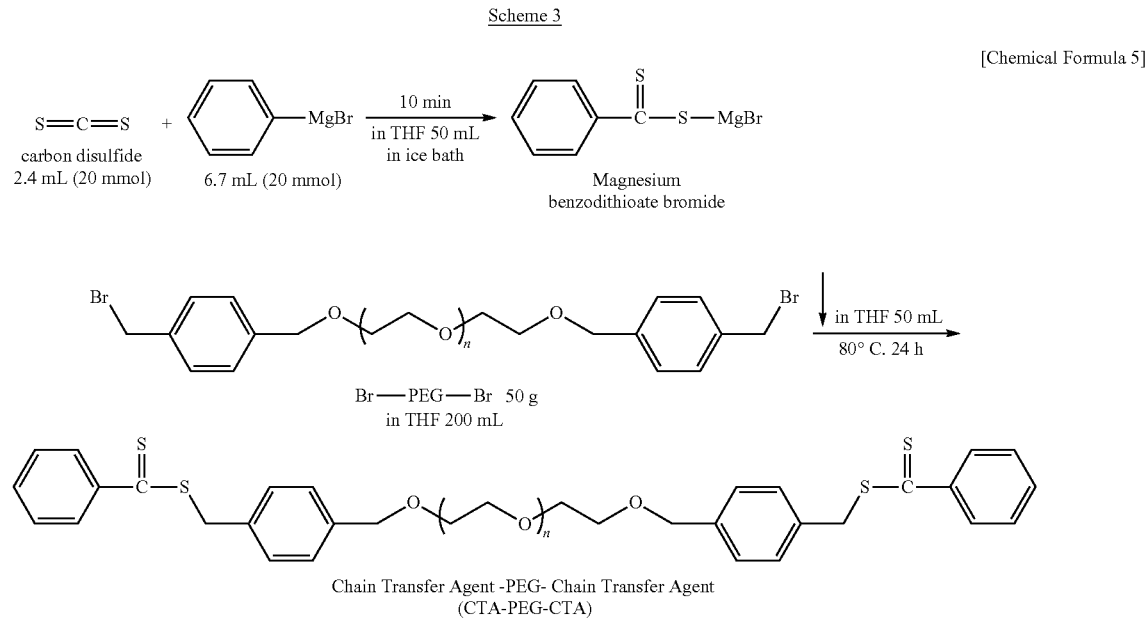

2.4 ml of carbon disulfide was added to 50 ml of THF. Next, magnesium benzothiobromide was obtained by gradually adding 6.7 ml (20 mmol) of benzyl magnesium bromide under ice cooling and allowing a reaction to progress. The target CTA (Chain Transfer Agent)-PEG-CTA (Chain Transfer Agent) was obtained by dissolving 50 g of the Br-PEG-Br synthesized in Production Example 14 in 200 mL of THF, adding the entire quantity of the prepared magnesium benzothiobromide, and allowing a reaction to progress at 60° C. for 24 hours. The obtained CTA-PEG-CTA was purified by being precipitated in 2-propanol and vacuum dried. The results of size exclusion chromatography (SEC) measurements and $^1$H-NMR spectral measurements for the obtained polymer are shown in FIG. 16.

<Production Example 16> Synthesis of polychloromethylstyrene-b-poly(ethylene glycol)-b-polychloromethylstyrene (PCMS-b-PEG-b-PCMS) Triblock Copolymer The PCMS-b-PEG-b-PCMS was synthesized according to Synthesis Scheme 4 shown below:

Scheme 4

[Chemical Formula 6]

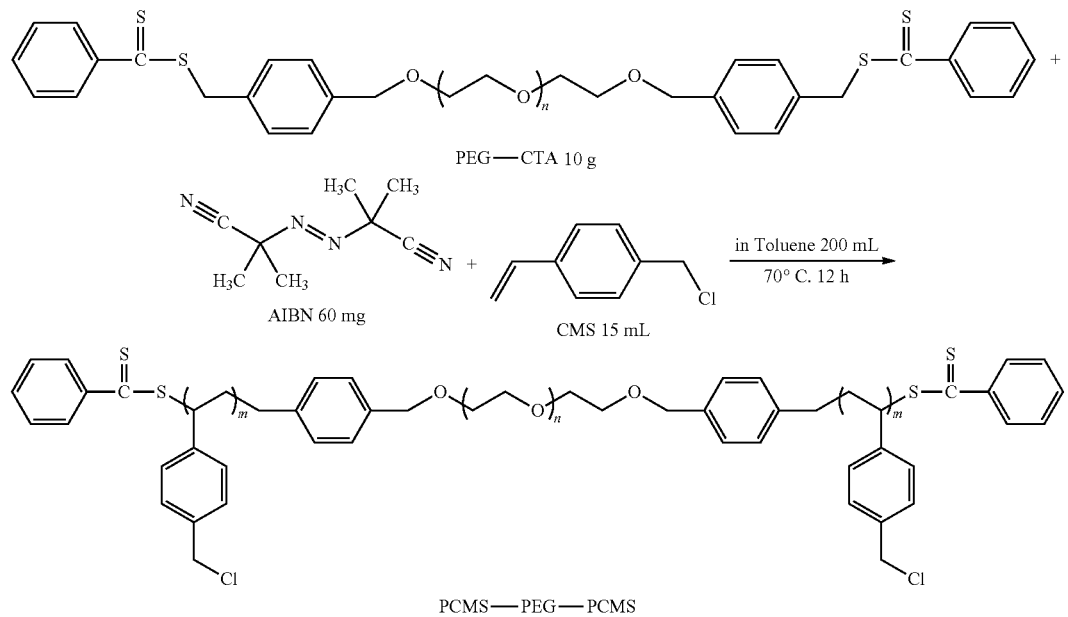

PEG—CTA 10 g

AIBN 60 mg

CMS 15 mL in Toluene 200 mL
70° C. 12 h

PCMS—PEG—PCMS

The target PCMS-b-PEG-b-PCMS was obtained by adding 10 g of the CTA-PEG-CTA synthesized in Production Example 15, 60 mg of azobisisobutyronitrile (AIBN) to 200 mL of toluene in a nitrogen atmosphere, adding 15 mL of chloromethylstyrene (CMS) and stirring at 60° C. for 24 hours. The obtained polymer was purified by being precipitated in 2-propanol and vacuum dried. The results of size exclusion chromatography (SEC) measurements and $^1$H-NMR spectral measurements for the obtained PCMS-b-PEG-b-PCMS are shown in FIG. 17.

<Production Example 17> Synthesis of triblock copolymer containing 2,2,6,6-tetramethylpiperidin-1-oxyl-4-yl (TEMPO) (PMNT-b-PEG-b-PMNT)

The PMNT-b-PEG-b-PMNT was synthesized according to Synthesis Scheme 5 shown below:

Scheme 5

[Chemical Formula 7]

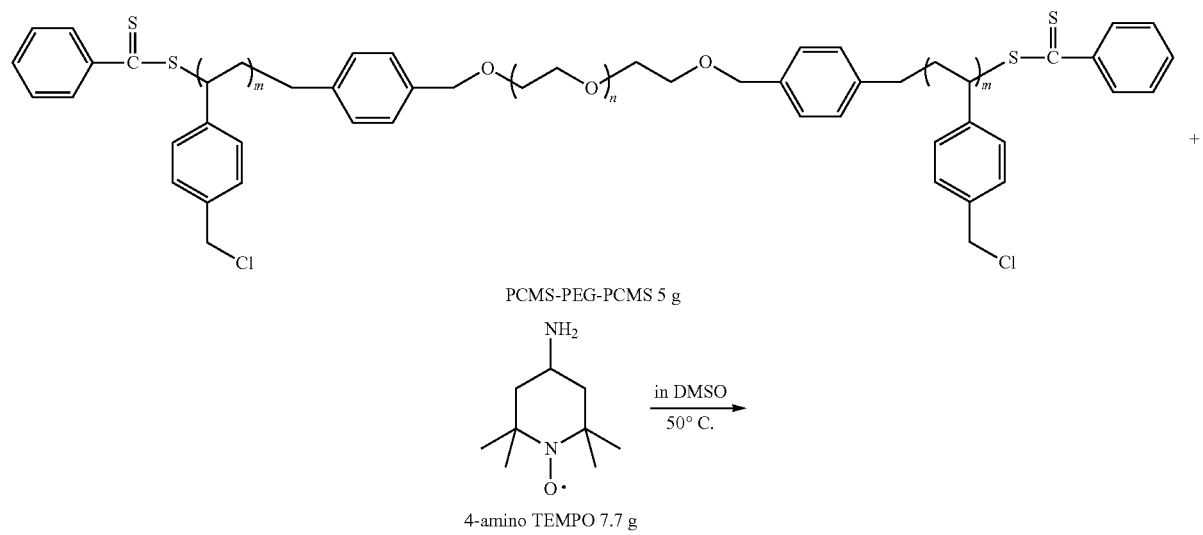

PCMS-PEG-PCMS 5 g 4-amino TEMPO 7.7 g in DMSO
50° C.

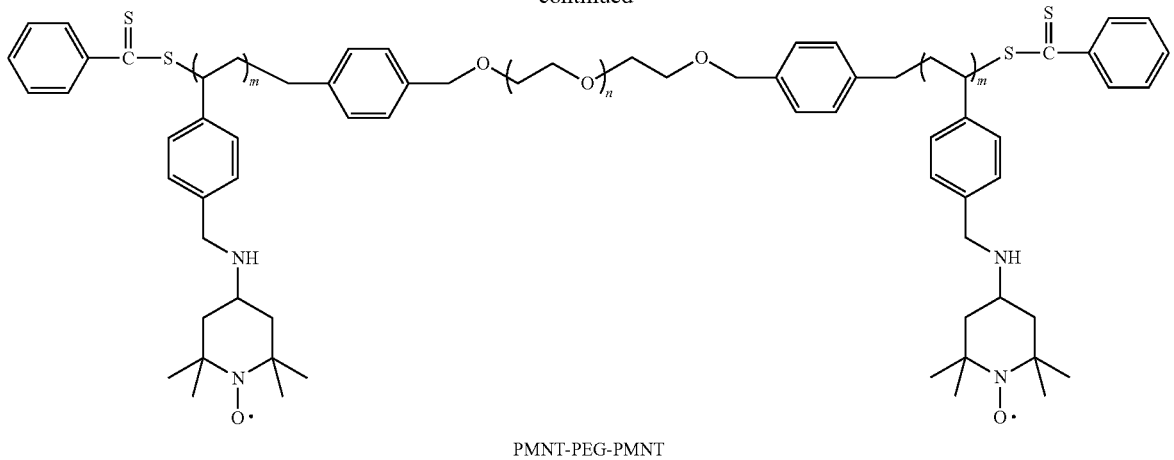

PMNT-PEG-PMNT

The target PMNT-b-PEG-b-PMNT was obtained by dissolving 5 g of the PCMS-b-PEG-b-PCMS synthesized in Production Example 16 and 7.7 g of 4-amino TEMPO in DMSO (dimethyl sulfoxide) and stirring at 50° C. so as to allow a reaction to progress. The obtained PMNT-b-PEG-b-PMNT was purified by being precipitated in 2-propanol and vacuum dried. The results of size exclusion chromatography (SEC) measurements and $^1$H-NMR spectral measurements for the obtained polymer are shown in FIG. 18.

<Production Example 18> Preparation of Polyion Complex Micelles 100 mg of the PMNT-b-PEG-b-PMNT triblock copolymer produced in Production Example 17 was dissolved in methanol, and 17.2 mg of PAAc (poly(acrylic acid)) dissolved in water was added to the obtained methanol solution. Next, polyion complex micelles were prepared by dialyzing this solution with water. When the average particle diameter of the obtained polyion complex micelles was measured by dynamic light scattering (DLS), it was confirmed that the polyion complex micelles were unimodal particles having an average particle diameter of 31 nm. (See FIG. 19)

The invention claimed is:

1. A composition comprising a triblock copolymer represented by formula (II), a polyanionic polymer and a physiologically active peptide:

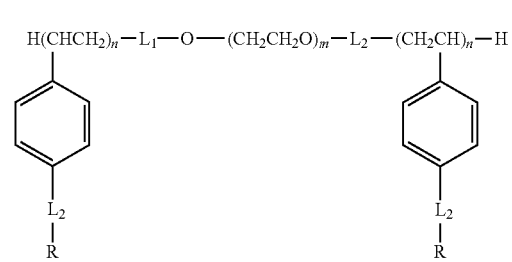

(II)

in the formula,
$L_1$ groups are linking groups that may be the same as, or different from, each other,
$L_2$ groups are each independently a —$C_{1-6}$ alkylene-NH—($C_{1-6}$ alkylene)q- group, with q being an integer of 0 or 1, wherein in at least one of the $L_2$ groups q=1,
R groups are each independently such that at least 50% of the total number (n) of R groups are residues of cyclic nitroxide radical compounds selected from the group consisting of 2,2,6,6-tetramethylpiperidin-1-oxyl-4-yl groups, 2,2,5,5-tetramethylpyrrolidin-1-oxyl-3-yl groups, 2,2,5,5-tetramethylpyrrolin-1-oxyl-3-yl groups, 2,4,4-trimethyl-1,3-oxazolidin-3-oxyl-2-yl groups, 2,4,4-trimethyl-1,3-thiazolidin-3-oxyl-2-yl groups and 2,4,4-trimethyl-imidazolidin-3-oxyl-2-yl groups, with the remaining R groups, when present, being hydrogen atoms, halogen atoms or hydroxyl groups,
terminal H groups may, in some cases, each independently be substituted by groups selected from among arylthiocarbonylthio groups, alkylthiocarbonylthio groups, alkoxythiocarbonylthio groups and sulfanyl groups,
m is an integer between 20 and 5,000, and
each instance of n is independently an integer between 3 and 1,000.

2. The composition according to claim 1, wherein the $L_1$ groups are each independently selected from the group consisting of single bonds, —S—(CH2)$_c$- groups, —S—(CH2)$_c$CO— groups, —(CH2)$_c$S— groups, —CO(CH2)$_c$S— groups, m- or p-phenylene groups, m- or p-xylylene groups and alkylene groups, c is an integer between 1 and 5, with these linking groups able to be in the opposite direction from that shown in formula (II) in cases where the linking groups are not directionally equivalent,
R is selected from among groups represented by the following formulae:

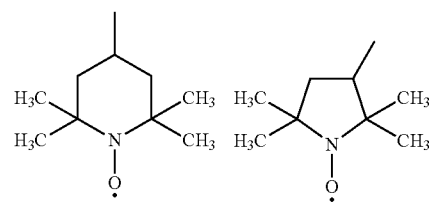

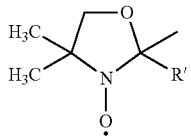

in the formulae, R' is a methyl group, and
at least 80% of the total number (n) of R groups are groups represented by the formula shown above.

3. The composition according to claim 1, wherein the polyanionic polymer is one or more types selected from the group consisting of poly(acrylic acid), poly(methacrylic acid), poly(sulfonic acid), polyanionic polysaccharides and anionic proteins.

4. The composition according to claim 1, wherein the physiologically active peptide is selected from the group consisting of enzyme proteins, antigenic proteins, antibodies, cytokines, peptide hormones and antimicrobial peptides.

5. The composition according to claim 1, wherein the ratio of a total anionic charge relative to a total cationic charge from the triblock copolymer, the polyanionic polymer and the physiologically active peptide is between 10:1 and 1:10 in an aqueous solution.

6. The composition according to claim 1, which is present as polyion complex micelles having an average particle diameter, as measured by a dynamic light scattering (DLS) method, of 10 to 300 nm in an aqueous solution.

7. The composition according to claim 1, which forms a gel according to changes in the ionic strength in the aqueous solution and/or changes in temperature.

8. A gel-forming medical composition comprising a polyion complex formed from the composition according to claim 1, and a pharmaceutically acceptable diluent or excipient.

9. A triblock copolymer represented by formula (II)

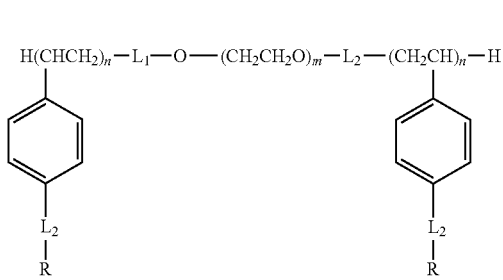

in the formula, $L_1$ groups are linking groups that may be the same as, or different from, each other, $L_2$ groups are each independently a $-C_{1-6}$ alkylene-NH—($C_{1-6}$ alkylene)q- group, with q being an integer of 0 or 1, wherein in at least one of the $L_2$ groups q=1, R groups are each independently such that at least 50% of the total number (n) of R groups are residues of cyclic nitroxide radical compounds selected from the group consisting of 2,2,6,6-tetramethylpiperidin-1-oxyl-4-yl groups, 2,2,5,5-tetramethylpyrrolidin-1-oxyl-3-yl groups, 2,2,5,5-tetramethylpyrrolin-1-oxyl-3-yl groups, 2,4,4-trimethyl-1,3-oxazolidin-3-oxyl-2-yl groups, 2,4,4-trimethyl-1,3-thiazolidin-3-oxyl-2-yl groups and 2,4,4-trimethyl-imidazolidin-3-oxyl-2-yl groups, with the remaining R groups, when present, being hydrogen atoms, halogen atoms or hydroxyl groups, terminal H groups are each substituted by groups selected from among arylthiocarbonylthio groups, alkylthiocarbonylthio groups, alkoxythiocarbonylthio groups and sulfanyl groups, m is an integer between 20 and 5,000, and each instance of n is independently an integer between 3 and 1,000.

10. The triblock copolymer according to claim 9, wherein the $L_1$ groups are each m- or p-phenylene groups, m- or p-xylylene groups or alkylene groups.

11. The composition according to claim 9, wherein the polyanionic polymer is one or more types selected from the group consisting of poly(acrylic acid), poly(methacrylic acid), poly(sulfonic acid), polyanionic polysaccharides and anionic proteins.

12. The composition according to claim 9, wherein the ratio of a total anionic charge relative to a total cationic charge from the triblock copolymer, the polyanionic polymer and the physiologically active peptide is between 10:1 and 1:10 in an aqueous solution.

13. A gel-forming medical composition comprising a polyion complex formed from the composition according to claim 9, and a pharmaceutically acceptable diluent or excipient.

* * * * *